United States Patent
Jeong et al.

(10) Patent No.: US 11,872,047 B2
(45) Date of Patent: Jan. 16, 2024

(54) BIO-SIGNAL DATA PROCESSING APPARATUS AND METHOD, AND COMPUTER PROGRAM FOR EXECUTING THE METHOD

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Soo A Lim, Seoul (KR)

(73) Assignee: ATSENS CO., LTD., Gyeonggi-do (KR)

(*) Notice: Subject to any disclaimer, the term of this patent is extended or adjusted under 35 U.S.C. 154(b) by 379 days.

(21) Appl. No.: 17/226,687

(22) Filed: Apr. 9, 2021

(65) Prior Publication Data
US 2022/0322991 A1 Oct. 13, 2022

(51) Int. Cl.
*G06F 15/16* (2006.01)
*A61B 5/333* (2021.01)
(Continued)

(52) U.S. Cl.
CPC ............ *A61B 5/333* (2021.01); *A61B 5/0006* (2013.01); *A61B 5/024* (2013.01); *A61B 5/308* (2021.01);
(Continued)

(58) Field of Classification Search
CPC ........... A61B 5/308; A61B 5/33; A61B 5/333; A61B 5/0006; A61B 5/024; A61B 5/7285; H04L 7/0041
(Continued)

(56) References Cited

U.S. PATENT DOCUMENTS 6,983,264 B2 * 1/2006 Shimizu ............ H04L 25/03165
706/22
8,483,809 B2 * 7/2013 Kim ...................... A61B 5/333
600/509
(Continued)

FOREIGN PATENT DOCUMENTS

KR    1020080004292    1/2008
KR    1020090034647    4/2009

OTHER PUBLICATIONS

Office action issued to corresponding Korean Application No. 1020190135605, dated Feb. 15, 2021.

*Primary Examiner* — Bharat Barot
(74) *Attorney, Agent, or Firm* — Guntin & Gust, PLC

(57) ABSTRACT

A bio-signal data processing apparatus includes a communicator configured to receive electrocardiogram data from a bio-signal measuring apparatus, a recording unit configured to record the electrocardiogram data, a transmission delay determiner, and an output information generator. The transmission delay determiner is configured to generate transmission delay information by comparing a recording time of the electrocardiogram data with a reception time of the electrocardiogram data, detect whether or not a delay according to data transmission occurs, by considering the transmission delay information, and, when the delay is detected to occur, calculating delay time information that is calculated on the basis of the transmission delay information. The output information generator is configured to correct the electrocardiogram data by using the delay time information and generate output data of the electrocardiogram data corresponding to a user input.

14 Claims, 9 Drawing Sheets

(51) Int. Cl.
  *A61B 5/00* (2006.01)
  *A61B 5/308* (2021.01)
  *A61B 5/024* (2006.01)
  *A61B 5/33* (2021.01)
  *H04L 7/00* (2006.01)

(52) U.S. Cl.
  CPC .............. *A61B 5/33* (2021.01); *A61B 5/7285* (2013.01); *H04L 7/0041* (2013.01)

(58) Field of Classification Search
  USPC .................. 709/248, 202–203, 217–219
  See application file for complete search history.

(56) References Cited

U.S. PATENT DOCUMENTS

| | | | |
|---|---|---|---|
| 11,432,779 B2* | 9/2022 | Kimbahune | A61B 5/7267 |
| 11,635,813 B2* | 4/2023 | Coleman | A61B 5/0024 |
| | | | 709/203 |
| 2014/0364701 A1* | 12/2014 | Masakov | A61B 5/333 |
| | | | 600/483 |
| 2018/0146921 A1* | 5/2018 | Yoon | A61B 5/681 |
| 2019/0110698 A1* | 4/2019 | Ko | A61B 5/02108 |
| 2021/0290139 A1* | 9/2021 | Yang | A61B 5/7267 |

* cited by examiner

BIO-SIGNAL DATA PROCESSING APPARATUS AND METHOD, AND COMPUTER PROGRAM FOR EXECUTING THE METHOD

BACKGROUND

1. Field

One or more embodiments of the present disclosure relate to a bio-signal data processing apparatus and method, and a computer program for executing the method.

2. Description of the Related Art

In order to maintain human life, there is a need for a process of enabling blood released by the heartbeat to flow along the arteries to all parts of the body without clogging and returning blood through the veins back to the heart. Accordingly, oxygen and nutrients may be supplied to the body's tissues, and consumed wastes may be removed through the metabolism.

However, when the human heart is in poor condition, blood may not be properly delivered to particular parts of the body or a blood clot or embolism may occur in the blood. As a result, blood may become cloudy, and the cloudy blood may block capillaries, in particular tissues of the body, and cause tissue necrosis, and thus, human life may be in danger. Therefore, in addition to clinical examinations, imaging tests and the like have been used to examine whether or not the heart is in an abnormal condition. Also, as an early diagnosis method, a method of determining whether or not a patient has an abnormality in the heart by measuring an electrocardiogram and displaying the measured electrocardiogram signal as a graph has also been widely used.

In other words, an electrocardiogram refers to recording, in a graph, a potential change in the surface of the body activating the mechanical activity of the heartbeat, such as contraction or expansion of the heart muscle. The electrocardiogram is a non-vascular test that is simple to measure, easily reproduced, easily repetitively recorded, and inexpensive to test. The electrocardiogram has been used helpfully to diagnose arrhythmia and coronary artery disease (cardiac artery disease) and monitor the progress of cardiac patients.

In general, the electrocardiogram is measured by attaching a sensor for measuring an electrocardiogram on the upper left and right and lower left and right of the chest and using a potential difference detected according to the location of the sensor.

SUMMARY

One or more embodiments according to the teachings of the present disclosure include a bio-signal data processing apparatus and method, the apparatus being attached to the body of a user to receive electrocardiogram data measured in real time, compensate the received electrocardiogram data for a delay occurring when the electrocardiogram data is transmitted, and output the compensated electrocardiogram data.

Additional aspects will be set forth in part in the description which follows and, in part, will be apparent from the description, or may be learned by practice of the presented embodiments of the disclosure.

According to one or more embodiments of the present disclosure, a bio-signal data processing apparatus includes: a communicator configured to receive bio-signal data from a bio-signal measuring apparatus; a recording unit configured to record the bio-signal data; a transmission delay determiner configured to generate transmission delay information based on a recording time of the bio-signal data and the bio-signal data, detect whether or not a delay according to data transmission occurs, by considering the transmission delay information, and, when the delay is detected to occur, calculate delay time information that is calculated on the basis of the transmission delay information; and an output information generator configured to correct the bio-signal data by using the delay time information and generate output data of the bio-signal data that is compensated for in response to a user input.

The recording time of the bio-signal data may be a time that is recorded through a time synchronization component of the bio-signal measuring apparatus.

The reception time of the bio-signal data may be a time at which the bio-signal data is received by the bio-signal data processing apparatus.

The transmission delay determiner may calculate time interval information between a first peak value and a second peak value included in the bio-signal data by using the delay time information and calculate a heart rate of the bio-signal data by using the time interval information.

The transmission delay determiner may extract a plurality of intervals included in the bio-signal data and calculate transmission delay information and time delay information for each of the intervals by calculating time interval information between peak values of the intervals.

The output information generator may generate output data of the bio-signal data by changing a time axis of bio-signal data of each of the intervals at a constant rate on the basis of the time delay information for each of the intervals of the bio-signal data.

The communicator may perform communication in a wireless communication method.

The communicator may receive bio-signal data via wireless communication and convert the bio-signal data to transmit the bio-signal data via wired communication.

The transmission delay determiner may generate a delay information table in which delay time information is recorded to correspond to set communication configuration information, generate initial delay time information by considering the delay information table, and calculate delay time information on the basis of newly calculated transmission delay information.

According to one or more embodiments of the present disclosure, a bio-signal data processing method of a bio-signal data processing apparatus including a communicator and a processor includes: receiving, by the bio-signal data processing apparatus, bio-signal data from a bio-signal measuring apparatus; recording, by the bio-signal data processing apparatus, the bio-signal data; generating, by the bio-signal data processing apparatus, transmission delay information based on a recording time of the bio-signal data and the bio-signal data, detecting whether or not a delay according to data transmission occurs, by considering the transmission delay information, and, when the delay is detected to occur, calculating delay time information that is calculated on the basis of the transmission delay information; and correcting, by the bio-signal data processing apparatus, the bio-signal data by using the delay time information and generating output data of the bio-signal data corresponding to a user input.

The recording time of the bio-signal data may be a time that is recorded through a time synchronization device of the bio-signal measuring apparatus.

The reception time of the bio-signal data may be a time at which the bio-signal data is received by the bio-signal data processing apparatus.

The calculating may include calculating time interval information between a first peak value and a second peak value included in the bio-signal data, by using the delay time information and calculating a heart rate of the bio-signal data by using the time interval information.

The calculating may include extracting a plurality of intervals included in the bio-signal data and calculating transmission delay information and time delay information for each of the intervals by calculating time interval information between peak values of the intervals.

The generating may include generating output data of the bio-signal data by changing a time axis of bio-signal data of each of the intervals at a constant rate on the basis of time delay information for each of the intervals of the bio-signal data.

The communicator may receive the bio-signal data in a wireless communication method.

The calculating may include generating a delay information table in which delay time information is recorded to correspond to set communication configuration information, generating initial delay time information by considering the delay information table, and calculating delay time information on the basis of newly calculated transmission delay information.

According to one or more embodiments, a computer program may be stored on a medium to execute, by using a computer, any one of methods of outputting electrocardiogram data according to one or more embodiments.

In addition, other methods and other systems for implementing one or more embodiments, and computer-readable recording media recording thereon a computer program for executing the method may be further included.

Although a computer is referred herein for convenience of description, various types of mobile electronic devices using one or more processors may also be included.

Other aspects, features, and advantages than those described above will become apparent from the following drawings, claims, and detailed description.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
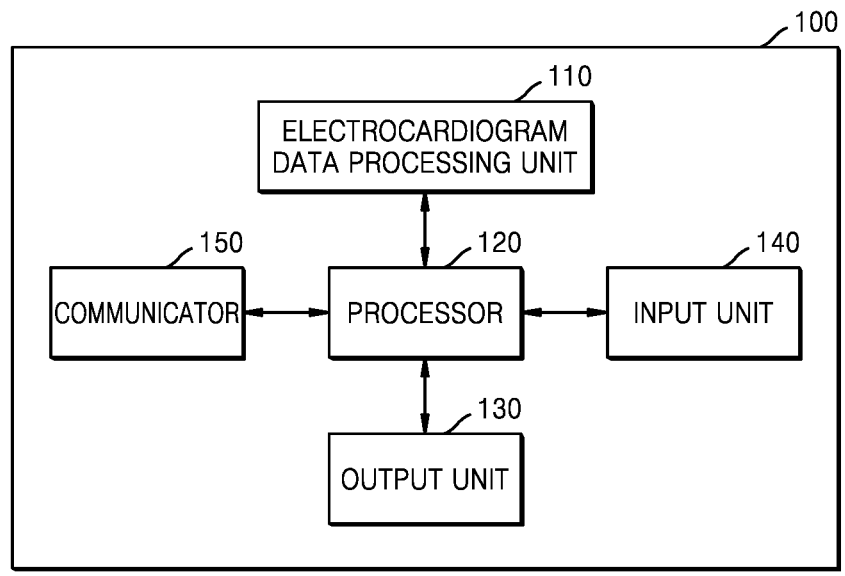
FIG. 1 is a block diagram of a bio-signal data processing apparatus according to one or more embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

The expressions "comprises," "includes," "may comprise," or "may include," etc. that may be used in various embodiments indicate the presence of disclosed corresponding functions, operations, elements, or the like but do not limit additional at least one function, operation, element, or the like. Also, it will be understood that the terms "comprises," "includes," "have," etc. when used herein, specify the presence of stated features, integers, steps, operations, elements, components, and/or combinations thereof but do not preclude the presence or addition of one or more other features, integers, steps, operations, elements, components, and/or combinations thereof.

In various embodiments, the expression "or" includes any and all combinations of words listed together. For example, "A or B" may include A, may include B, or may include both A and B.

The expressions, such as "first", "second" used in various embodiments, may modify various components of various embodiments but do not limit the corresponding components. For example, the above expressions do not limit the order and/or importance of the corresponding components. The above expressions may be used to distinguish one element or component from another element or component. For example, a first user device and a second user device are both user devices and represent different user devices. For example, a first element or component could be termed a second element or component, and, similarly, a second element or component could be termed a first element or component without departing from the scope of various embodiments.

When an element or component is referred to as being "coupled to" or "connected to" another element or component, it may be directly coupled to or connected to the other element or component, or intervening elements or components may be present. In contrast, when an element or component is referred to as being "directly coupled to" or "directly connected to" another element or component, intervening elements or components may not be present.

As used herein, the terms "module", "unit", "part", etc. refers to an element or component that performs at least one function or operation, and these elements or components may be implemented as hardware, software, or a combination of hardware and software. In addition, "a plurality of modules", "units", "parts", etc. may be integrated into at least one module or chip and implemented as at least one processor, except when each needs to be implemented as individual particular hardware.

The terminology used in various embodiments is for the purpose of describing particular embodiments only and is not intended to be limiting and/or restricting of various embodiments. The singular forms are intended to include the plural forms as well, unless the context clearly indicates otherwise.

Unless otherwise defined, all terms including technical or scientific terms used herein have the same meaning as commonly understood by one of ordinary skill in the art to which various embodiments belong.

It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, various embodiments will be described in detail with reference to the accompany drawings.

As used herein, a bio-signal refers to a signal including data such as body temperature, a pulse, an electrocardiogram, a brain wave, a respiratory rate, a step count, stress, hormones, exercise amount, burned calories, body fat, body water, a blood sugar value, blood pressure, and the like.

FIG. 1 is a block diagram of a bio-signal data processing apparatus 100 according to one or more embodiments.

The bio-signal data processing apparatus 100 refers to a computing apparatus connected to a bio-signal measuring apparatus via a communication network to receive bio-signal data including electrocardiogram data and the like. The bio-signal data processing apparatus 100 may include input/output units, one or more processors, communicators, and a memory and may include one or more processors. The bio-signal data processing apparatus 100 may receive bio-signal data including electrocardiogram data and the like by executing instructions stored in the memory connected thereto electrically or via a communication network.

The bio-signal data processing apparatus 100 may generate bio-signal data including electrocardiogram data and the like in which a delay occurring according to a transmission environment is corrected or compensated for. The bio-signal data processing apparatus 100 may be implemented to output bio-signal data including received electrocardiogram data and/or compensated electrocardiogram data. The bio-signal data processing apparatus 100 may be implemented to generate instructions and/or control signals for outputting bio-signal data and transmit the commands/or control signals to an external output device. Electrocardiogram data may be measured by a bio-signal measuring apparatus and transmitted to the bio-signal data processing apparatus 100. Transmission and the like of electrocardiogram data may be processed by a request from the bio-signal data processing apparatus 100 or a user input which is input into the bio-signal measuring apparatus. Electrocardiogram data may be transmitted to the bio-signal data processing apparatus 100 in an environment where a time delay or a delay occurs according to a communication protocol, a version of communication protocol, a type of communication network, a communication environment, a transmission speed, the specifications or performance of the bio-signal data processing apparatus 100, and the like when the electrocardiogram data is transmitted from the bio-signal measuring apparatus to the bio-signal data processing apparatus 100. The bio-signal data processing apparatus 100 may correct or compensate electrocardiogram data to remove a delay acquired from electrocardiogram data measured in an environment changing in real time during transmission of data and accurately extract, from the corrected electrocardiogram data, a heart rate, an R wave feature, and the like of a person to be diagnosed. The bio-signal data processing apparatus 100 may be implemented to output the compensated electrocardiogram data and/or extracted heart rate, R wave feature, and the like of a person to be diagnosed.

A processor 120 is a component for overall control of the bio-signal data processing apparatus 100 and may include one or more processors. In detail, the processor 120 controls overall operation of the bio-signal data processing apparatus 100 by using various types of functions and programs stored in an electrocardiogram data processing unit 110 of the bio-signal data processing apparatus 100.

For example, the processor 120 may include a CPU, RAM, ROM, and a system bus. Here, the ROM is a component in which a set of instructions for system booting is stored, and the CPU copies, a stored operating system (O/S) of an electronic device, to the RAM according to instructions stored in the ROM and executes the O/S to boot a system. When booting is completed, the CPU may copy various types of stored applications to the RAM and execute the applications to perform various types of operations. As described above, the bio-signal data processing apparatus 100 includes only one CPU but may be implemented to include a plurality of CPUs (or a digital signal processor (DSP), a separate function block, and the like).

The processor 120 may be implemented as a DSP, a microprocessor, or a time controller (TCON). However, the processor 120 is not limited thereto and may include one or more of a central processing unit (CPU), a microcontroller unit (MCU), a micro processing unit (MPU), a controller, an application processor (AP), a communication processor (CP), and an ARM processor or may be defined by a corresponding term. In addition, the processor 120 may be implemented as a System on Chip (SoC) or large scale integration (LSI) having a processing algorithm therein, or may be implemented in the form of a field programmable gate array (FPGA).

An output unit 130 may display information which is generated by the electrocardiogram data processing unit 110. According to one embodiment, the output unit 130 may display a user interface for a user input which is input via an input unit 140. The output unit 130 may output stored graphic data, visual data, auditory data, and vibration data under control of the electrocardiogram data processing unit 110.

The output unit 130 may be implemented as various types of display panels. For example, a display panel may be implemented via various display technologies such as a liquid crystal display (LCD), an organic light-emitting diode (OLED) display, an active-matrix organic light-emitting diode (AM-OLED) display, a liquid crystal on silicon (LcoS) display, a digital light processing (DLP) display, and the like. In addition, the output unit 130 may be coupled, in the form of a flexible display, to at least one of a front area, a side area, and a rear area of a display panel.

The output unit 130 may also have an input function. For example, the output unit 130 may be implemented as a touchscreen having a layer structure. A touchscreen may have a display function, a function of detecting a touch input location, a touched area, and touch input pressure, and a function of detecting a real touch and a proximity touch.

The input unit 140 may include a user interface for inputting various types of information to the bio-signal data processing apparatus 100.

A communicator 150 is a component for transmitting and receiving data to and from a device such as a server or another electronic device. The communicator 150 may include a wireless network, a wired network, or the like or may have a plurality of transmission and reception channels and a combination of wired and wireless networks. The communicator 150 may be connected to one or more bio-signal measuring apparatuses 200 by requests from the one or more bio-signal measuring apparatuses 200 or by a user input.

The bio-signal data processing apparatus 100 may further include a storage medium (not shown) which stores various types of data for overall operation, such as a program for processing or control of the processor 120. The storage medium may store a plurality of application programs or applications driven in the bio-signal data processing apparatus 100, and pieces of data and instructions for operation of the bio-signal data processing apparatus 100. At least some of the application programs may be downloaded from an external server via wired or wireless communication. In addition, at least some of the application programs may be present, for basic functions of the bio-signal data processing apparatus 100, on the bio-signal data processing apparatus 100 from the release time thereof. The application programs may be stored in the storage medium and may be driven by the processor 120 to perform operation (a function) of the bio-signal data processing apparatus 100.

Figure 2:
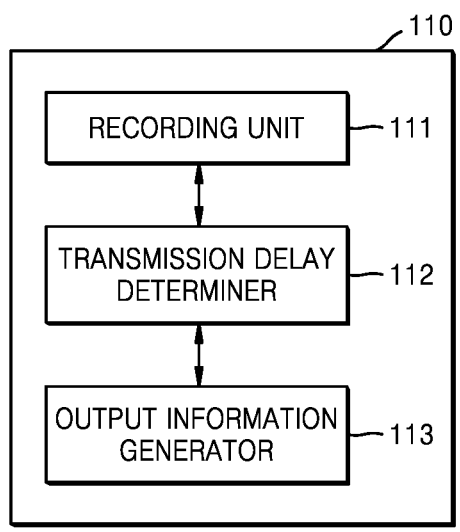
FIG. 2 is a block diagram of an electrocardiogram data processing unit of a bio-signal data processing apparatus.

FIG. 2 is a block diagram of the electrocardiogram data processing unit 110.

The electrocardiogram data processing unit 110 may include a recording unit 111, a transmission delay determiner 112, and an output information generator 113.

The recording unit 111 receives electrocardiogram data from the communicator 150 and records the electrocardiogram data. The received electrocardiogram data may include time information (a time, a date, and the like) recorded (measured) by the bio-signal measuring apparatus 200. The recorded time information refers to information measured by a time synchronization component (a timer or the like) of the bio-signal measuring apparatus 200.

The transmission delay determiner 112 may generate transmission delay information based on a recording time of electrocardiogram data and the electrocardiogram data. The transmission delay determiner 112 may generate transmission delay information by comparing a recording time of electrocardiogram data and the electrocardiogram data. The transmission delay determiner 112 may detect whether or not a delay according to data transmission occurs, by considering the transmission delay information. The reception time may include information about a point in time at which the electrocardiogram data is received by the bio-signal data processing apparatus 100. For example, transmission delay information is information associated with a time delay and/or a delay, according to transmission, detected by comparing electrocardiogram data measured by the bio-signal data processing apparatus 100 with associated data that occurs and is generated by the bio-signal measuring apparatus 200 when receiving the electrocardiogram data. For example, the associated data that occurs or is generated by the bio-signal measuring apparatus 200 may include at least one of information about a time at which electrocardiogram data is received through a communication channel, information about a time at which some intervals of the electrocardiogram data are received through the communication channel, and information about a time at which measurement points of the electrocardiogram data are received through the communication channel.

For example, transmission delay information may be generated by comparing a first time difference value between a first recording time and a second recording time included in electrocardiogram data with a second time difference value between a first reception time corresponding to a first recording time and a second reception time corresponding to a second recording time, wherein the first reception time and the second reception time are measured through the bio-signal data processing apparatus 100. The first recording time and/or the second recording time refer to time information that is acquired and recorded by the timer of the bio-signal measuring apparatus 100. The first reception time and/or the second reception time refer to time information acquired by a timer of the bio-signal data processing apparatus 100. The transmission delay information may be set, as true, as to whether or not a transmission delay occurs when a difference is great by comparing the first time difference value to the second time difference value. In this case, delay time information may be calculated as much as the difference between the first and second time difference values.

In another embodiment, transmission delay information may be generated by comparing a $1$-$1^{th}$ peak value and a $1$-$2^{th}$ peak value included in electrocardiogram data with a $2$-$1^{th}$ peak value and a $2$-$2^{th}$ peak value included in received electrocardiogram data. Whether or not a transmission delay occurs and delay time information may be calculated by comparing a time difference value between a recording time of the $1$-$1^{th}$ peak value and a recording time of the $1$-$2^{th}$ peak value with a time difference value between the $2$-$1^{th}$ peak value and the $2$-$2^{th}$ peak value. A peak value may be detected by considering a voltage value, a current value, and the like of an electrocardiogram signal.

In detail, the transmission delay determiner 112 may generate the transmission delay information by comparing first interval information between the $1$-$1^{th}$ peak value and the $1$-$2^{th}$ peak value included in the electrocardiogram data with second interval information between the $2$-$1^{th}$ peak value and the $2$-$2^{th}$ peak value. The $1$-$2^{th}$ peak value may be a $K^{th}$ peak value after the $1$-$1^{th}$ peak value, and the $2$-$2^{th}$ peak value may be a $L^{th}$ peak value after the $2$-$1^{th}$ peak value. K and L may be the same integer.

When the transmission delay determiner 112 detects that a delay occurs, the transmission delay determiner 112 may calculate delay time information that is calculated on the basis of transmission delay information.

The transmission delay determiner 112 may receive electrocardiogram data according to n heart rates and additionally receive a first average interval value between n particular signals of the electrocardiogram data, for example, between R peak values. The transmission delay determiner 112 may calculate a second average interval value between n particular signals included in received electrocardiogram data, for example, between R peak values and calculate transmission delay information and/or delay time information by comparing the first average interval value to the second average interval value. The first average interval value may be set as a reference average interval value to be applied to calculate a transmission delay of consecutively received electrocardiogram data.

The transmission delay determiner 112 may generate transmission delay information by considering a first total length of time of electrocardiogram data having n heart rates and a second total length of time at which the electrocardiogram data is received. In this case, the transmission delay determiner 112 may calculate delay time information by using Equation below.

delay value=length of time for second heartbeat−
length of time for first heartbeat (average)
length of time for second heartbeat=second total
length of time (unit of time)/n (average) length
of time for first heartbeat=first total length of
time (unit of time)/n When a delay value falls within a preset range, transmission delay information may be set as true, and the delay value may be set as delay time information.

The output information generator 113 may correct electrocardiogram data and a heart rate of the electrocardiogram data by using delay time information and generate output data of the electrocardiogram data corresponding to a user input. A heart rate of received electrocardiogram data may be corrected on the basis of a reference heart rate and delay time information.

The output information generator 113 may compensate electrocardiogram data and a heart rate of the electrocardiogram data on the basis of delay time information to generate compensated electrocardiogram data.

Here, for convenience of description, a function is executed by an internal block of the electrocardiogram data processing unit 110. However, the electrocardiogram data processing unit 110 may include only a program capable of processing a function, and the actual execution of the function may be performed by the processor 120.

Figure 3:
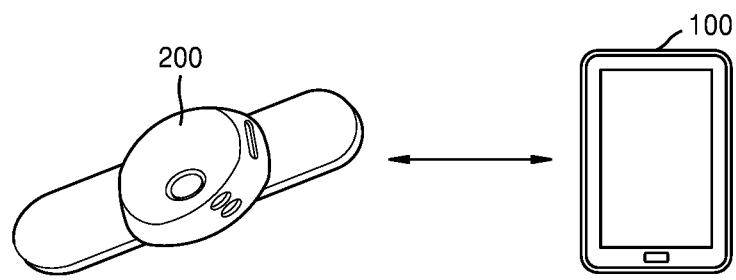
FIG. 3 is a view of a network environment connected to an apparatus for measuring an electrocardiogram.
Figure 4A:
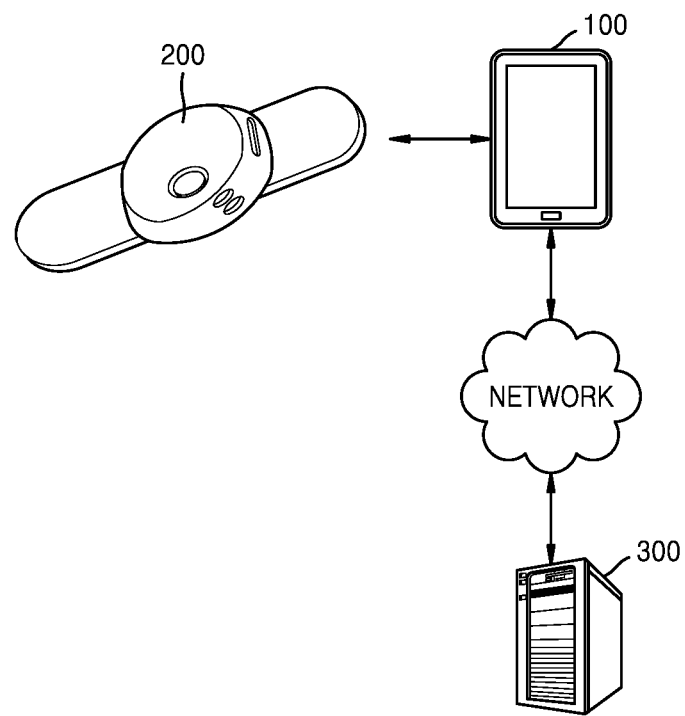
FIG. 4A illustrates another network environment connected to the apparatus for measuring an electrocardiogram.
Figure 4B:
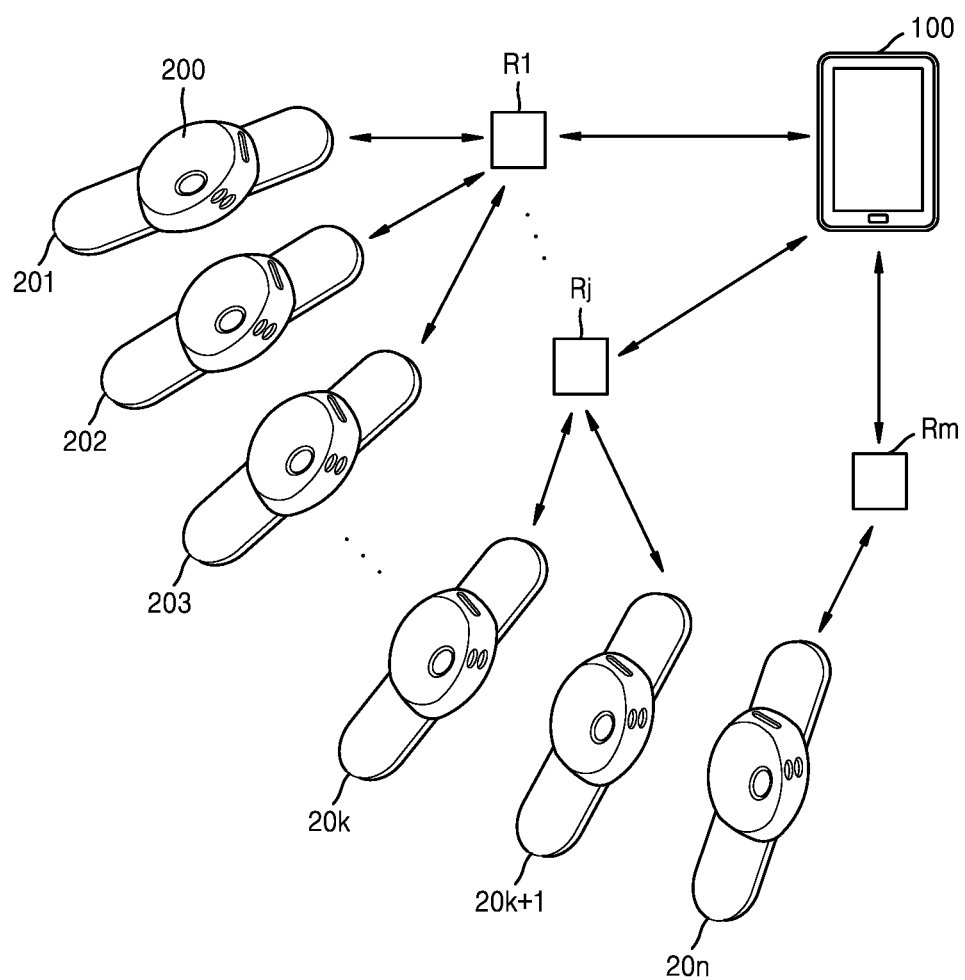
FIG. 4B illustrates further another network environment connected to the apparatus for measuring an electrocardiogram.

FIGS. 3, 4A, and 4B are views for explaining an operation of transmitting and receiving data between a bio-signal measuring apparatus 200 and a bio-signal data processing apparatus 100, according to one or more embodiments. Here, wireless communication inevitable includes data transmission delay. And data latency is non-uniform among data. In a case of 10 msec latency tolerance in BLE (Bluetooth Low Energy), timing information of the receiving electrocardiogram data is distorted.

The bio-signal data processing apparatus 100 may compensate electrocardiogram data received from the bio-signal measuring apparatus 200 for a transmission delay. The bio-signal data processing apparatus 100 may be used in a small electronic device or the like such as a mobile phone, a smartphone, a laptop computer, a digital broadcasting terminal, a personal digital assistant (PDA), a portable multimedia player (PMP), a navigation device, an MP3 player, an electric toothbrush, an electronic tag, a lighting device, a remote controller, a fishing bobber, or a wearable device but is not limited thereto. A computing device having one or more processors, a distributed computing device, a server, or the like may be included. The bio-signal data processing apparatus 100 is illustrated as an electronic device including a display, as shown in FIG. 3, but may be a computing apparatus that does not include an output device.

The bio-signal data processing apparatus 100 may establish a communication connection to the bio-signal measuring apparatus 200 via a near field communication method and receive, from the bio-signal measuring apparatus 200, electrocardiogram data measured in real time. A reception time of the bio-signal data processing apparatus 100 for electrocardiogram data may be delayed due to an increase in a communication distance to the bio-signal measuring apparatus 200, a degradation of the specifications and communication performance of the bio-signal data processing apparatus 100, a degradation of a communication performance of the bio-signal measuring apparatus 200, and the like, and the bio-signal data processing apparatus 100 may output electrocardiogram data by calculating delay time information for the delay of the reception time.

The bio-signal data processing apparatus 100 may generate transmission delay information by comparing information included in received electrocardiogram data with information obtained by measuring, by a provided timer, information about a time at which the electrocardiogram data is received. When electrocardiogram data is received with a certain time difference, the bio-signal data processing apparatus 100 determines that a transmission delay does not occur. In contrast, when the bio-signal data processing apparatus 100 detects that an event for changing information about a time at which electrocardiogram data is received, information about an interval between peak values included in the electrocardiogram data, or the like has occurred, the bio-signal data processing apparatus 100 may determine that a transmission delay has occurred. In other words, electrocardiogram data measured by the bio-signal measuring apparatus 200 is measured at certain time intervals, and, when time information of electrocardiogram data received by the bio-signal data processing apparatus 100 is not kept constant, the bio-signal data processing apparatus 100 may detect that a delay according to transmission of the electrocardiogram data has occurred.

The bio-signal measuring apparatus 200 may be attached to the human body to measure electrocardiogram data of one or more channels via a plurality of electrodes. The bio-signal measuring apparatus 200 may receive electrocardiogram measurement data of one or more channels measured by an external electrode, and the number of electrocardiogram measurement channels may extend. The bio-signal measuring apparatus 200 may transmit, to the bio-signal data processing apparatus 100, an electrocardiogram, which is measured according to a preset period, in preset n units. The bio-signal data processing apparatus 100 may also receive, from the bio-signal measuring apparatus 200, a control signal associated with measurement, transmission, and the like of electrocardiogram data.

The bio-signal data processing apparatus 100 may be implemented to receive electrocardiogram data from a plurality of bio-signal measuring apparatuses 200. The bio-signal data processing apparatus 100 may calculate transmission delay information for each bio-signal measuring apparatus. The bio-signal data processing apparatus 100 may be implemented to include only one or more processors and a memory. Operations of the bio-signal data processing apparatus 100 may be executed by executing a program stored in the provided memory.

As shown in FIG. 4A, the bio-signal data processing apparatus 100 may compensate and output electrocardiogram data received from the bio-signal measuring apparatus 200, transmit the received electrocardiogram data to an electrocardiogram management server 300, and further transmit, to the electrocardiogram management server 300, information associated with compensation for the electrocardiogram data. The compensation for a delay according to transmission of electrocardiogram data has been described as being processed by the bio-signal data processing apparatus 100 but may be processed by the electrocardiogram management server 300. In addition, the bio-signal measuring apparatus 200 may directly transmit electrocardiogram data to the electrocardiogram management server 300 to allow the electrocardiogram data to be processed by the electrocardiogram management server 300.

The electrocardiogram management server 300 may manage, in association with an object, the electrocardiogram data received from the bio-signal data processing apparatus 100. The electrocardiogram management server 300 may store electrocardiogram data of a first object in relation to the first object.

According to another embodiment, the bio-signal measuring apparatus 200 may communicate with the bio-signal data processing apparatus 100 through a repeater (not shown).

FIG. 4B is a view for explaining a network environment in which a bio-signal data processing apparatus 100 communicates with a plurality of bio-signal measuring apparatuses 201, 202, 203, 20$k$, 20$k$+1, and 20$n$.

When communication environments between the bio-signal measuring apparatuses 201, 202, 203, 20$k$, 20$k$+1, and 20$n$ and the bio-signal data processing apparatus 100 are not uniform, a bio-signal may be transmitted by using a plurality of repeaters R1, R$j$, and R$m$. The bio-signal data processing apparatus 100 may communicate with the bio-signal measuring apparatuses 201, 202, 203, 20$k$, 20$k$+1, and 20$n$ having various types of transmission delays by using the plurality of repeaters R1, R$j$, and R$m$. Accordingly, the non-uniformity of a transmission delay of a bio-signal to be processed may increase.

The bio-signal data processing apparatus 100 may directly receive bio-signals from one or more of the bio-signal measuring apparatuses 201, 202, 203, 20$k$, 20$k$−1, and 20$n$. The bio-signal data processing apparatus 100 may receive, through one or more of the repeaters R1, R$j$, and R$m$, bio-signals generated by one or more of the bio-signal measuring apparatuses 201, 202, 203, 20$k$, 20$k$+1, and 20$n$. On the basis of communication environments of the bio-signal measuring apparatuses 201, 202, 203, 20$k$, 20$k$+1, and 20$n$, the bio-signal measuring apparatuses 201, 202, and 203 communicating with a first transmission delay may transmit bio-signals to the bio-signal data processing apparatus 100 through the repeater (or a first repeater) R1, the bio-signal measuring apparatuses 20$k$ and 20$k$+1 communicating with a $j^{th}$ transmission delay may transmit bio-signals to the bio-signal data processing apparatus 100 through the repeater (or a $j^{th}$ repeater) R$j$, and the bio-signal measuring apparatus 20$n$ communicating with a $m^{th}$ transmission delay may transmit a bio-signal to the bio-signal data processing apparatus 100 through the repeater (or a $m^{th}$ repeater) R$m$. The bio-signal measuring apparatuses 201, 202, 203, 20$k$, 20$k$+1, and 20$n$ may determine repeaters for relaying transmission of bio-signals on the basis of distances to the bio-signal data processing apparatus 100, communication environments, the degrees of transmission delays, and the like and transmit bio-signals through the determined repeaters. The bio-signal data processing apparatus 100 may compensate bio-signals, which are received through one of a plurality of repeaters, for a transmission delay to the same degree.

Figure 5:
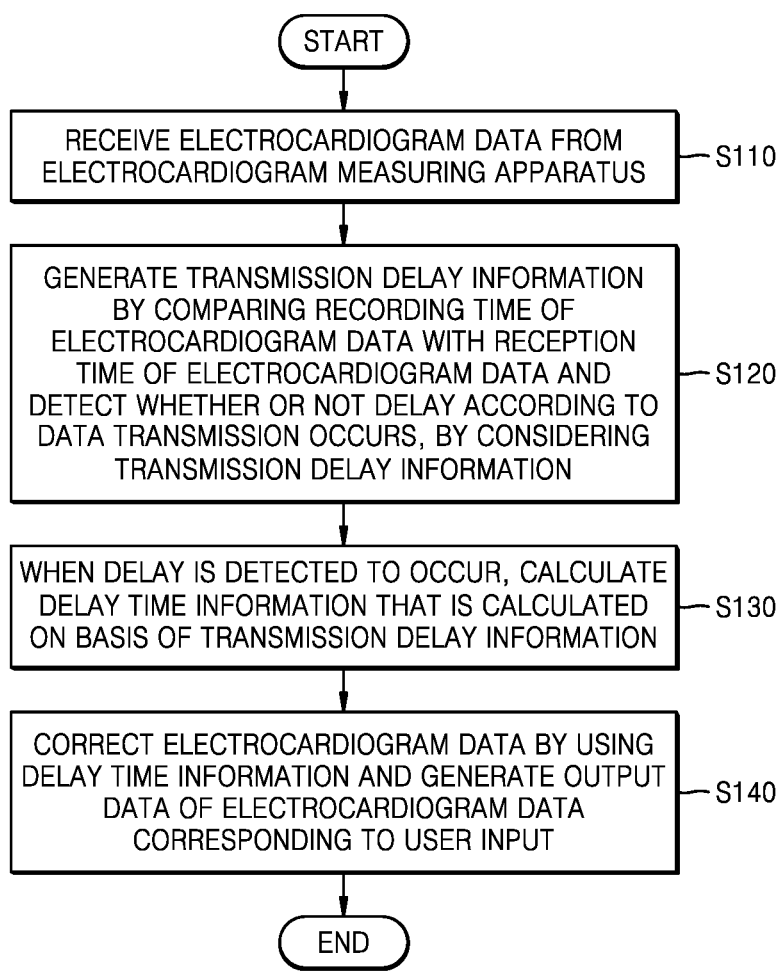
FIG. 5 is a flowchart of a method of outputting electrocardiogram data, according to a first embodiment.
Figure 6:
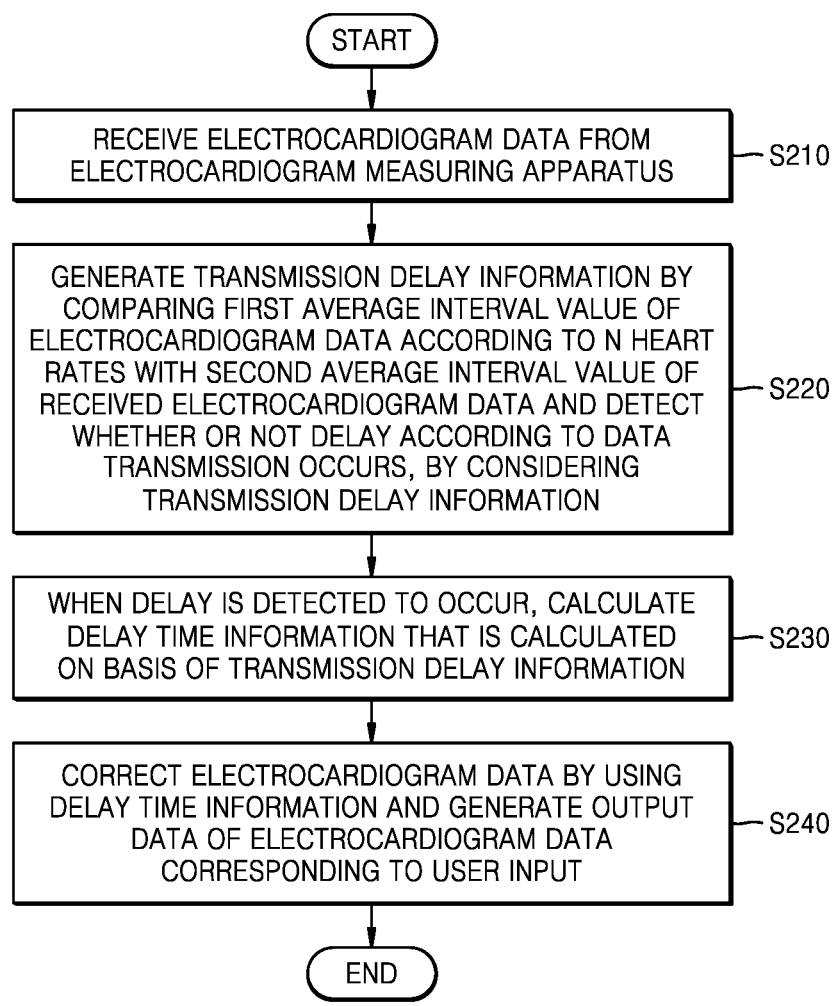
FIG. 6 is a flowchart of a method of outputting electrocardiogram data, according to a second embodiment.

FIGS. 5 and 6 are flowcharts of a method of outputting electrocardiogram data, according to one or more embodiments. More specifically, FIG. 5 is a flowchart of a method of outputting electrocardiogram data according to a first embodiment;

FIG. 6 is a flowchart of a method of outputting electrocardiogram data, according to a second embodiment.

In operation S110, the bio-signal data processing apparatus 100 may receive, from a bio-signal measuring apparatus, a bio-signal including electrocardiogram data and the like.

In another embodiment, the bio-signal data processing apparatus 100 may receive a bio-signal of the bio-signal measuring apparatus through a repeater.

In operation S120, the bio-signal data processing apparatus 100 may generate transmission delay information by comparing a recording time of the electrocardiogram data with a reception time of the electrocardiogram data and detect whether or not a delay according to data transmission occurs, by considering the transmission delay information. For example, transmission delay information is information associated with a delay, according to transmission, detected by comparing electrocardiogram data measured by the bio-signal measuring apparatus with associated data generated when receiving the electrocardiogram data.

For example, transmission delay information may be generated by comparing a first time difference value between a first recording time and a second recording time included in electrocardiogram data with a second time difference value between a first reception time corresponding to a first recording time and a second reception time corresponding to a second recording time. The first reception time and the second reception time are measured through the bio-signal data processing apparatus 100. The first recording time and/or the second recording time refer to time information acquired and recorded by a timer of the bio-signal measuring apparatus. The first reception time and/or the second reception time refer to time information acquired by a timer of the bio-signal data processing apparatus 100. The transmission delay information may be set, as true, as to whether or not a transmission delay occurs when a difference is great by comparing the first time difference value to the second time difference value, and delay time information may be calculated as much as the difference between the first and second time difference values.

In another embodiment, transmission delay information may be generated by comparing a 1-$1^{th}$ peak value and a 1-$2^{th}$ peak value included in electrocardiogram data with a 2-$1^{th}$ peak value and a 2-$2^{th}$ peak value included in received electrocardiogram data, respectively. Whether or not a transmission delay occurs and delay time information may be calculated by comparing a time difference value between a recording time of the 1-$1^{th}$ peak value and a recording time of the 1-$2^{th}$ peak value with a time difference value between the 2-$1^{th}$ peak value and the 2-$2^{th}$ peak value. A peak value may be detected by considering a voltage value, a current value, and the like of an electrocardiogram signal.

In detail, the bio-signal data processing apparatus 100 may generate transmission delay information by comparing first interval information between a 1-$1^{th}$ peak value and a 1-$2^{th}$ peak value included in electrocardiogram data with second interval information between a 2-$1^{th}$ peak value and a 2-$2^{th}$ peak value included in electrocardiogram data.

In operation S130, when the bio-signal data processing apparatus 100 detects that the delay occurs, the bio-signal data processing apparatus 100 may calculate delay time information that is calculated on the basis of transmission delay information.

In operation S140, the bio-signal data processing apparatus 100 may correct the electrocardiogram data by using the delay time information and generate output data of the electrocardiogram data corresponding to a user input.

In operation S210, the bio-signal data processing apparatus 100 may receive electrocardiogram data from a bio-signal measuring apparatus.

In operation S220, the transmission delay determiner 112 of the bio-signal data processing apparatus 100 may receive electrocardiogram data according to n heart rates and additionally receive a first average interval value between n particular signals of the electrocardiogram data, for example, between R peak signals. The transmission delay determiner 112 may calculate a second average interval value between n particular signals included in the received electrocardiogram data, for example, between R peak signals, and calculate transmission delay information and delay time information by comparing the first average interval value to the second average interval value. The first average interval value may be received only once and set as a reference average interval value to be applied to calculate a transmission delay of consecutively received electrocardiogram data.

The transmission delay determiner 112 may generate transmission delay information by considering a first total length of time for electrocardiogram data having n heart rates and a second total length of time for which the electrocardiogram data is received. In this case, the transmission delay determiner 112 may calculate delay time information by using Equation below.

delay time information=length of time for second heartbeat−length of time for first heartbeat (average) length of time for second heartbeat=second total length of time (unit of time)/$n$ (average) length of time for first heartbeat=first total length of time (unit of time)/$n$ In operation S230, when the bio-signal data processing apparatus 100 detects that the delay occurs, the bio-signal data processing apparatus 100 may calculate delay time information that is calculated on the basis of transmission delay information.

In operation S240, the bio-signal data processing apparatus 100 may correct the electrocardiogram data by using the delay time information and generate output data of the electrocardiogram data corresponding to a user input.

FIGS. 7 through 9 illustrate a process of compensating electrocardiogram data by the bio-signal data processing apparatus 100.

Figure 7A:
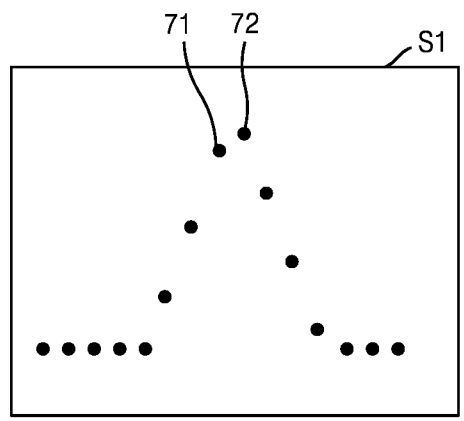
FIG. 7A is a diagram of measured value.
Figure 7B:
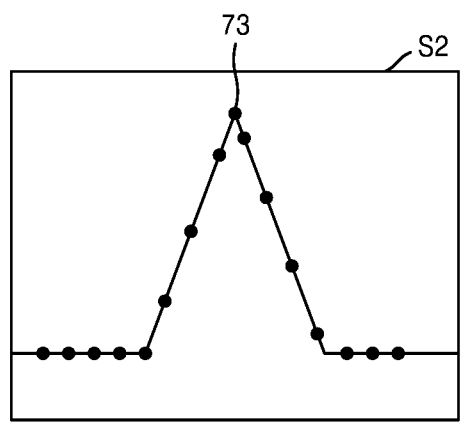
FIG. 7B is a diagram of electrocardiogram data.
Figure 7C:
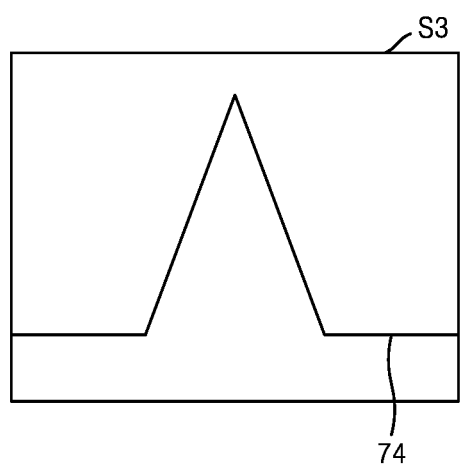
FIG. 7C is a diagram of an electrocardiogram pattern generated based on electrocardiogram data.

FIG. 7A is a diagram of measured value, FIG. 7B is a diagram of electrocardiogram data, and FIG. 7C is a diagram of an electrocardiogram pattern generated based on electrocardiogram data.

The electrocardiogram data processing apparatus 100 may receive electrocardiogram data 51 and generate electrocardiogram data S2 corresponding to a peak 73, on the basis of pieces of received electrocardiogram data. The received electrocardiogram data 51 may include electrocardiogram signals that are measured at certain time intervals. The electrocardiogram signals may be measured at the same time interval.

The bio-signal data processing apparatus 100 may generate output data S3 that is converted into two-dimensional line data 74 by connecting pieces of electrocardiogram data S2 having a compensated peak, as shown in FIG. 7C.

Figure 8A:
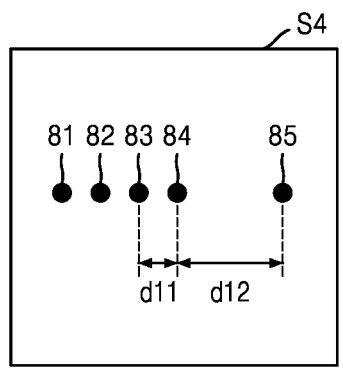
FIG. 8A is a diagram of electrocardiogram data with a transmission delay time.
Figure 8B:
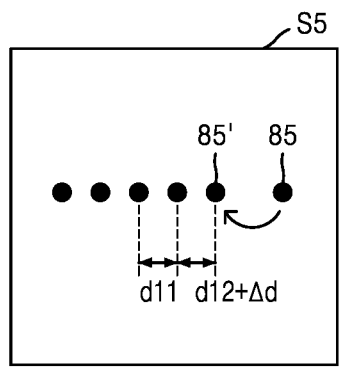
FIG. 8B is a diagram for describing electrocardiogram data compensated based on a transmission delay time.

FIG. 8A is a diagram of electrocardiogram data with a transmission delay time, and FIG. 8B is a diagram for describing electrocardiogram data compensated based on a transmission delay time.

As shown in FIG. 8A, received electrocardiogram data S4 may include electrocardiogram signals represented by dots such as 81, 82, 83, 84, and 85. The electrocardiogram signals may be expressed as intervals of recording times. The electrocardiogram signals may be measured at preset time intervals and may be implemented to be measured at the same time interval. A time interval d11 between the electrocardiogram signals 83 and 84 of the electrocardiogram signals and a time interval d12 of the electrocardiogram signals 84 and 85 may be compared with each other, and transmission delay information Δd that is present at the time interval d12 between the electrocardiogram signals 84 and 85 may be calculated. The bio-signal data processing apparatus 100 may correct the electrocardiogram signal 85 to an electrocardiogram signal 85' on the basis of the transmission delay information Δd, as shown in FIG. 8B.

Figure 9A:
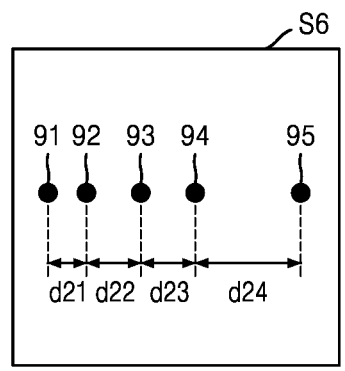
FIG. 9A is a diagram of electrocardiogram data with a transmission delay time.
Figure 9B:
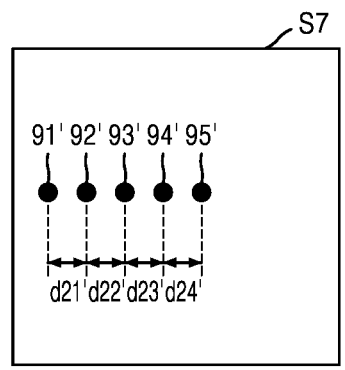
FIG. 9B is a diagram for explaining the calculation of transmission delay time.

FIG. 9A is a diagram of electrocardiogram data with a transmission delay time, and FIG. 9B is a diagram for explaining the calculation of transmission delay time.

As shown in FIG. 9A, when electrocardiogram data including electrocardiogram signals 91, 92, 93, 94, and 95 and first, second, third, and fourth time intervals d21, d22, d23, and d24 is received, the first time interval d21 may be compared with the second, third, and fourth time intervals d22, d23, and d24 to generate electrocardiogram signals 91', 92', 93', 94', and 95' having time intervals d21', d22', d23', and d24' that are compensated for the first, second, third, and fourth time intervals d21, d22, d23, and d24, respectively, as shown in FIG. 9B.

Figure 10A:
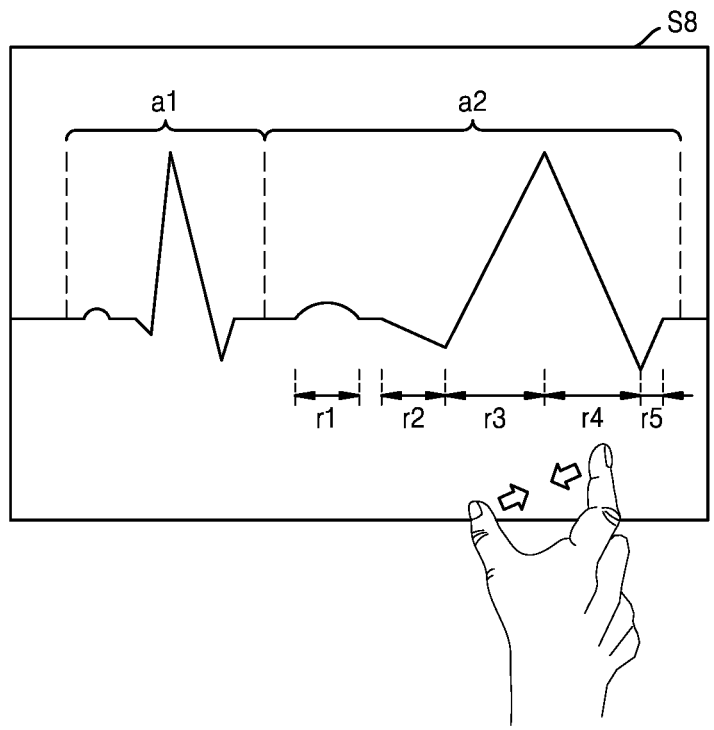
FIG. 10A is a diagram explaining that an electrocardiogram pattern is adjusted by a user input.
Figure 10B:
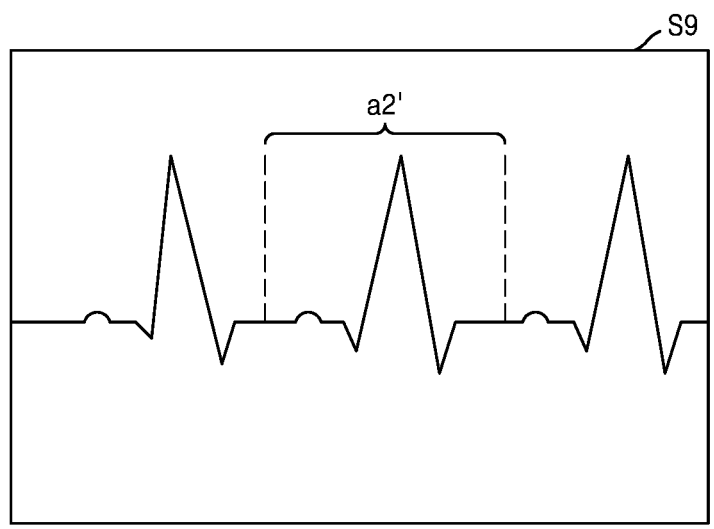
FIG. 10B is a diagram explaining an output screen of electrocardiogram data.

FIGS. 10A and 10B are views illustrating output information for electrocardiogram data generated by the bio-signal data processing apparatus 100.

When electrocardiogram data is received as in S8, the bio-signal data processing apparatus 100 may generate transmission delay information for an interval a2 by comparing intervals a1 and a2. The bio-signal data processing apparatus 100 may respond to a user input for narrowing a time interval to change r1, r2, r3, r4, and r5 of the interval a2 according to time information of the interval a1 to thereby change the interval a2 to an interval a2' of S9, as shown in FIG. 10B.

Apparatuses as described above may be implemented as hardware components, software components, and/or a combination of hardware components and software components. For example, apparatuses and components described in one or more embodiments may be implemented by using one or more general purpose computers or special purpose computers such as a processor, a controller, an arithmetic logic unit (ALU), a digital signal processor, a microcomputer, a field programmable gate array (FPGA), a programmable logic unit (PLU), a microprocessor, or any other apparatuses capable of executing and responding to instructions. A processing unit may execute an operating system (OS) and one or more software applications executed on the OS. In addition, the processing unit may access, store, manipulate, process, and generate data in response to the execution of software. For convenience of description, one processing unit may be described as being used, but one of ordinary skill in the art may understand that the processing unit may include a plurality of processing elements and/or a plurality of types of processing elements. For example, the processing unit may include a plurality of processors or one processor and one controller. Also, the processing unit may include another processing configuration such as a parallel processor.

Software may include a computer program, code, instructions, or a combination of one or more thereof, and configure the processing unit to operate as wanted or independently or collectively instruct the processing unit. Software and/or data may be permanently or temporarily embodied in any type of machine, a component, a physical device, virtual equipment, a computer storage medium or device, or transmitted signal waves to be interpreted by the processing unit or to provide the processing unit with instructions or data.

The software may be distributed over networked computer systems to be stored or executed in a distributed manner. The software and data may be stored on one or more computer-readable recording media.

The method according to the embodiments may be embodied in the form of program instructions that may be executed through various types of computer means and then recorded on a computer-readable recording medium. The computer-readable recording medium may include program instructions, data files, data structures, and the like alone or in combination. The program instructions recorded on the computer-readable recording medium may be particularly designed and configured for the embodiments or may be well known to and used by one of ordinary skill in the computer software art. Examples of the computer-readable recording medium include magnetic media such as a hard disk, a floppy disk, and a magnetic tape, optical media such as a CD-ROM and a DVD, magneto-optical media such as a floptical disk, and a hardware device particularly configured to store and execute program instructions such as ROM, RAM, flash memory, and the like. Examples of the program instructions include not only machine language code generated by a compiler, but also high-level language code that may be executed by a computer by using an interpreter or the like. The hardware device described above may be configured to operate as one or more software modules so as to perform operations of the embodiments, and the reverse thereof is the same.

According to one or more embodiments, in accordance with the above-described necessity, an apparatus may be attached to the body of a user to receive electrocardiogram data measured in real time, compensate for a delay occurring when transmitting the received electrocardiogram data, and output the compensated electrocardiogram data.

Although the embodiments have been described above by limited embodiments and drawings, various modifications and changes may be made from the above description by one of ordinary skill in the art. For example, the described techniques may be performed in a different order than the described method, and/or components of the described system, structure, device, circuit, and the like may be combined or joined in a different form than the described method, or even if replaced or substituted by other components or equivalents, and an appropriate result may be achieved.

Therefore, other embodiments, other aspects, and equivalents to the claims also belong to the scope of the claims that will be described below.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A bio-signal data processing apparatus comprising:
   a communicator configured to receive electrocardiogram data measured in real time from a bio-signal measuring apparatus, wherein the measured electrocardiogram data include a first recording time and a second recording time;
   a recording unit configured to record one or more reception times of the electrocardiogram data received from the bio-signal measuring apparatus, wherein the one or more reception times further include a first reception time corresponding to the first recording time and a second reception time corresponding to the second recording time;
   a transmission delay determiner configured to:
      generate transmission delay information by comparing a first time difference value between the first recording time and the second recording time of the electrocardiogram data and a second time difference value between the first reception time and the second reception time;
      detect whether or not a delay according to data transmission occurs based on the transmission delay information; and
      when the delay is detected to have occurred, calculate delay time information based on a difference value between the first time difference value and the second time difference value; and
   an output information generator configured to compensate for the electrocardiogram data by using the delay time information and generate output data of the compensated electrocardiogram data based on the delay time information.

2. The bio-signal data processing apparatus of claim 1, wherein the first reception time and the second reception time of the electrocardiogram data correspond to a time at which the electrocardiogram data is received by a timer of the bio-signal data processing apparatus.

3. The bio-signal data processing apparatus of claim 1, wherein the transmission delay determiner:
   extracts a plurality of intervals included in the electrocardiogram data; and
   calculates the transmission delay information and the delay time information for each of the plurality of intervals by calculating time interval information between peak values of the intervals.

4. The bio-signal data processing apparatus of claim 3, wherein the output information generator generates the output data of the compensated electrocardiogram data by changing a time axis of the electrocardiogram data of each of the plurality of intervals at a constant rate on the basis of the time delay information for each of the intervals of the electrocardiogram data.

5. The bio-signal data processing apparatus of claim 1, wherein the communicator performs communication in a wireless communication method.

6. The bio-signal data processing apparatus of claim 5, wherein the communicator receives the electrocardiogram data via wireless communication and converts the electrocardiogram data to transmit the electrocardiogram data via wired communication.

7. The bio-signal data processing apparatus of claim 1, wherein the transmission delay determiner:
   generates a delay information table in which the delay time information is recorded to correspond to set communication configuration information;
   generates initial delay time information by considering the delay information table; and
   calculates new delay time information on the basis of newly calculated transmission delay information.

8. A bio-signal data processing method of a bio-signal data processing apparatus comprising a communicator and a processor, the bio-signal data processing method comprising steps of:
   receiving by the bio-signal data processing apparatus, electrocardiogram data measured in real time from a bio-signal measuring apparatus, wherein the measured electrocardiogram data include a first recording time and a second recording time;

recording, by the bio-signal data processing apparatus, one or more reception times of the electrocardiogram data received from the bio-signal measuring apparatus, wherein the one or more reception times further include a first reception time corresponding to the first recording time and a second reception time corresponding to the second recording time;

generating, by the bio-signal data processing apparatus, transmission delay information by comparing a first time difference value between the first recording time and the second recording time of the electrocardiogram data and a second time difference value between the first reception time and the second reception time of the electrocardiogram data;

detecting whether or not a delay according to data transmission occurs, based on the transmission delay information;

when the delay is detected to have occurred, calculating delay time information based on a difference value between the first time difference value and the second time difference value;

compensating, by the bio-signal data processing apparatus, the electrocardiogram data by using the delay time information; and generating output data of the compensated electrocardiogram data based on the delay time information.

9. The bio-signal data processing method of claim 8, wherein the first reception time and the second reception time of the electrocardiogram data is a time at which the electrocardiogram data is received by the bio-signal data processing apparatus.

10. The bio-signal data processing method of claim 8, further comprising:

extracting a plurality of intervals included in the electrocardiogram data; and calculating the transmission delay information and the delay time information for each of the plurality of intervals by calculating time interval information between peak values of the intervals.

11. The bio-signal data processing method of claim 10, wherein the generating the output data of the compensated electrocardiogram data further includes generating the output data of the compensated electrocardiogram data by changing a time axis of bio-signal data of each of the plurality of intervals at a constant rate on the basis of time delay information for each of the plurality of intervals of the electrocardiogram data.

12. The bio-signal data processing method of claim 8, wherein the communicator receives the electrocardiogram data in a wireless communication method.

13. The bio-signal data processing method of claim 8, further comprising:

generating a delay information table in which the delay time information is recorded to correspond to set communication configuration information;

generating initial delay time information by considering the delay information table; and calculating new delay time information on the basis of newly calculated transmission delay information.

14. A non-transitory computer-readable recording medium storing therein an operating program that causes a computer to execute a process comprising:

receiving, by a bio-signal data processing apparatus, electrocardiogram data measured in real-time from a bio-signal measuring apparatus, wherein the measured electrocardiogram data include a first recording time and a second recording time;

recording, by the bio-signal data processing apparatus, one or more reception times of the electrocardiogram data received from the bio-signal measuring apparatus, wherein the one or more reception times further include a first reception time corresponding to the first recording time and a second reception time corresponding to the second recording time;

generating, by the bio-signal data processing apparatus, transmission delay information by comparing a first time difference value between the first recording time and the second recording time of the electrocardiogram data and a second time difference value between the first reception time and the second reception time of the electrocardiogram data;

detecting whether or not a delay according to data transmission occurs, based on the transmission delay information, and when the delay is detected to have occurred, calculating delay time information based on the a difference value between the first time difference value and the second time difference value; and compensating, by the bio-signal data processing apparatus, the electrocardiogram data based on the delay time information; and generating output data of the compensated electrocardiogram data.

* * * * *